United States Patent

Cantatore et al.

Patent Number: 5,134,233
Date of Patent: Jul. 28, 1992

[54] PIPERIDINE-TRIAZINE COMPOUNDS CONTAINING SILANE GROUPS

[75] Inventors: Giuseppe Cantatore, Bitonto; Valerio Borzatta, Bologna; Graziano Vignali, Sasso Marconi, all of Italy

[73] Assignee: Ciba-Geigy Corporation, Ardsley, N.Y.

[21] Appl. No.: 709,687

[22] Filed: Jun. 3, 1991

[30] Foreign Application Priority Data

Jun. 6, 1990 [IT] Italy .................. 20556 A/90

[51] Int. Cl.$^5$ .................. C07D 401/12; C07F 7/10
[52] U.S. Cl. .................. 544/198; 544/113; 544/219; 544/83; 544/209; 544/212; 540/598
[58] Field of Search .............. 540/598; 544/198, 212, 544/209, 113, 219, 83

[56] References Cited

U.S. PATENT DOCUMENTS

| | | | |
|---|---|---|---|
| 2,949,434 | 8/1960 | Bailey et al. | 524/101 |
| 4,086,204 | 4/1978 | Cassandrini et al. | 544/182 |
| 4,108,829 | 8/1978 | Cassandrini et al. | 544/218 |
| 4,177,186 | 12/1979 | Rody et al. | 546/14 |
| 4,859,759 | 8/1989 | Maycock et al. | 546/14 |
| 4,946,880 | 8/1990 | Costanzi et al. | 524/99 |
| 4,948,888 | 8/1990 | Greco et al. | 544/69 |
| 5,039,799 | 8/1991 | Cantatore et al. | 544/113 |

FOREIGN PATENT DOCUMENTS

0162524 11/1985 European Pat. Off. .
0343717 11/1989 European Pat. Off. .

Primary Examiner—John M. Ford
Attorney, Agent, or Firm—Luther A. R. Hall

[57] ABSTRACT

The present invention relates to novel piperidine-triazine compounds containing silane groups of the formula (I)

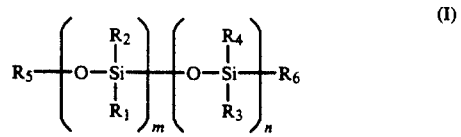

in which $R_1$ is a group of the formula

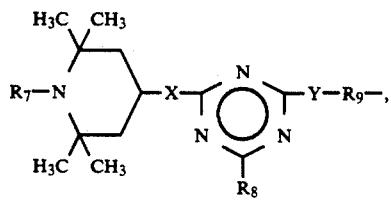

$R_7$ is e.g. hydrogen, X is e.g. $>N-R_{10}$ with $R_{10}$ being $C_1-C_4$alkyl, $R_8$ is e.g. a group of the formula

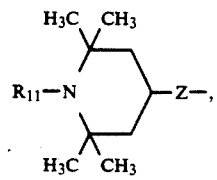

with $R_{11}$ being hydrogen and Z being as defined for X; Y is e.g. $>NH$, $R_9$ is e.g. trimethylene, $R_2$ is e.g. methyl, ethoxy or OH, $R_3$ and $R_4$ are e.g. $C_1-C_6$alkyl or phenyl, m+n is a number from 1 to 100, n is zero or a number from 1 to 90 and can vary from zero to 90% of the sum of m+n, $R_5$ is e.g. ethyl and $R_6$ is e.g. ethoxy, and, when m+n is a number from 3 to 10, $R_5$ and $R_6$ together can also form a direct bond.

These compounds are effective as stabilizers for organic materials.

8 Claims, No Drawings

PIPERIDINE-TRIAZINE COMPOUNDS CONTAINING SILANE GROUPS

The present invention relates to novel piperidine-triazine compounds containing silane groups, to their use as light stabilizers, heat stabilizers and oxidation stabilizers for organic materials, in particular synthetic polymers, and to organic materials thus stabilized.

It is known to use triazine compounds containing 2,2,6,6-tetramethylpiperidyl groups as stabilizers for synthetic polymers, for example those claimed in U.S. Pat. No. 4,086,204.

2,2,6,6-Tetramethylpiperidine derivatives containing silane groups are also known, such as those reported in U.S. Pat. Nos. 4,177,186, 4,946,880 and 4,948,888 and European laid open prints 162,524 and 343,717.

The present invention relates to novel compounds of the general formula (I)

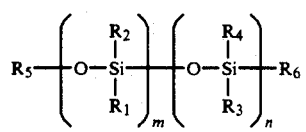

in which $R_1$ is a group of the formula (II)

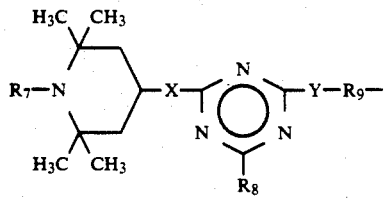

where $R_7$ is hydrogen, $C_1$-$C_8$alkyl, O, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl; or $C_1$-$C_8$acyl, X is —O— or >N—$R_{10}$, where $R_{10}$ is hydrogen, $C_1$-$C_{18}$alkyl, $C_2$-$C_4$alkyl substituted in the 2-, 3- or 4-position by $C_1$-$C_8$alkoxy, by di-($C_1$-$C_4$alkyl)-amino or by a 5-membered to 7-membered nitrogen containing heterocyclic group with the free valency on the nitrogen atom; $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; tetrahydrofurfuryl or a group of the formula (III)

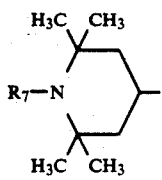

with $R_7$ as defined above, or X can also be a 1,4-piperazinediyl group or a group of the formula (IVa) or (IVb)

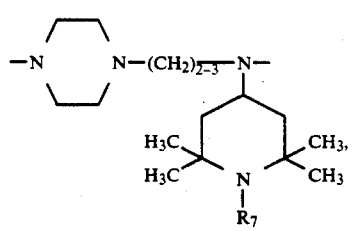

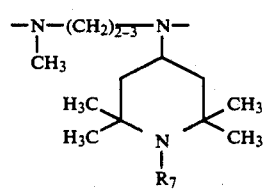

with $R_7$ as defined above and the nitrogen atom substituted by the piperidyl group being bound to the triazine ring of the group of the formula (II), $R_8$ is one of the groups of the formulae (Va)–(Vd)

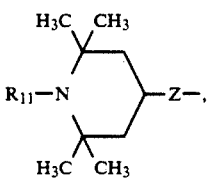

in which $R_{11}$ is as defined for $R_7$, Z is as defined for X, and $R_{12}$, $R_{13}$ and $R_{14}$ which can be identical or different are hydrogen, $C_1$-$C_{18}$alkyl, $C_2$-$C_4$alkyl substituted in the 2-, 3- or 4-position by $C_1$-$C_8$alkoxy, by di-($C_1$-$C_4$alkyl)-amino or by a 5-membered to 7-membered nitrogen containing heterocyclic group with the free valency on the nitrogen atom; $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; or tetrahydrofurfuryl, or $R_{13}$ is OH or $C_1$-$C_8$alkoxy, or

is a 5-membered to 7-membered heterocyclic group, $R_9$ is $C_1$-$C_{12}$alkylene or $C_5$-$C_{15}$alkylene interrupted by 1 or 2 groups of the formula (VI)

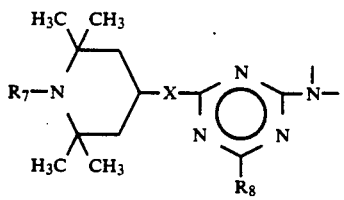 (VI)

with $R_7$, $R_8$ and X as defined above and Y is a group >N—$R_{15}$ where $R_{15}$ is hydrogen, $C_1$-$C_{18}$alkyl, $C_5$-$C_{12}$cycloalkyl which is unsubstituted or mono-, di- or tri-substituted by $C_1$-$C_4$alkyl; or $C_7$-$C_9$phenylalkyl which is unsubstituted or mono-, di- or tri-substituted on the phenyl by $C_1$-$C_4$alkyl; or Y, when $R_9$ is $C_1$-$C_{12}$alkylene, can also be —O— or —S—, $R_2$ is $C_1$-$C_8$alkyl, $C_1$-$C_8$alkoxy, OH, ONa or OK, $R_3$ and $R_4$ which can be identical or different are $C_1$-$C_8$alkyl or phenyl, m+n is a number from 1 to 100, n is zero or a number from 1 to 90 and can vary from zero to 90% of the sum of m+n, $R_5$ is hydrogen, $C_1$-$C_8$alkyl, Na, K or a group $(R_{16})_3$Si— with $R_{16}$ being $C_1$-$C_8$alkyl, and $R_6$ is $C_1$-$C_8$alkoxy, OH, ONa, OK or a group $(R_{16})_3$SiO— with $R_{16}$ as defined above and, when m+n is a number from 3 to 10, $R_5$ and $R_6$ together can also form a direct bond.

Each of the groups $R_1$, $R_2$, $R_3$ and $R_4$ can have the same definition or different definitions in the recurring structural units contained in formula (I) and, when the compounds of the present invention are copolymeric, they can have a random distribution or a block distribution of the individual structural units.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by $C_1$-$C_8$alkoxy, preferably $C_1$-$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of $C_2$-$C_4$alkyl substituted by a 5-membered to 7-membered nitrogen containing heterocyclic group are the groups of the formula

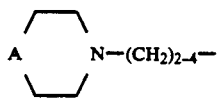

in which A is a direct bond, —O—, —$CH_2$— or —$CH_2CH_2$—. The group

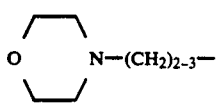

is preferred.

Examples of alkoxy having not more than 18 carbon atoms are methoxy, ethoxy, propoxy, isopropoxy, butoxy, isobutoxy, pentoxy, isopentoxy, hexoxy, heptoxy, oxtoxy, decyloxy, dodecyloxy, tetradecyloxy, hexadecyloxy and octadecyloxy.

Examples of $C_5$-$C_{12}$cycloalkyl which is unsubstituted or mono-, di- or tri-substituted by $C_1$-$C_4$alkyl, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred.

Representative examples of $C_5$-$C_{12}$cycloalkoxy $R_7$ and $R_{11}$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, hexenyl, decenyl, undecenyl and oleyl. Those alkenyls are preferred in which the carbon atom in the 1-position is saturated. Allyl is particularly preferred.

Representative examples of phenyl $R_{12}$, $R_{13}$ and $R_{14}$ which is mono-, di- or tri-substituted by $C_1$-$C_4$alkyl or $C_1$-$C_4$alkoxy are methylphenyl, dimethylphenyl, trimethylphenyl, t-butylphenyl, di-t-butylphenyl, 3,5-di-t-butyl-4-methylphenyl, methoxyphenyl and ethoxyphenyl.

Examples of $C_7$-$C_9$phenylalkyl which is unsubstituted or mono-, di- or tri-substituted on the phenyl by $C_1$-$C_4$alkyl are benzyl, methylbenzyl, dimethylbenzyl, trimethylbenzyl, t-butylbenzyl and 2-phenylethyl. Benzyl is preferred.

Acyl $R_7$ and $R_{11}$ containing not more than 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonoyl. $C_1$-$C_8$alkanoyl, $C_3$-$C_8$alkenoyl and benzoyl are preferred. Acetyl is especially preferred.

A 5-membered to 7-membered heterocyclic group

can contain a further heteroatom, for example nitrogen or oxygen; representative examples are 1-pyrrolidyl, 1-piperidyl, 4-morpholinyl, 4-methyl-1-piperazinyl and 1-hexahydroazepinyl. 4-Morpholinyl is preferred.

Examples of $C_1$-$C_{12}$alkylene are methylene, ethylene, propylene, trimethylene, 2-methyltrimethylene, tetramethylene, pentamethylene, hexamethylene, octamethylene, decamethylene, undecamethylene and dodecamethylene. Trimethylene is preferred.

Examples of $C_5$-$C_{15}$alkylene interrupted by 1 or 2 groups of the formula (VI) are the groups —($CH_2$)$_{2-6}$—Q—($CH_2$)$_3$— and —($CH_2$)$_{2-6}$—Q—($CH_2$)$_{2-6}$—Q—($CH_2$)$_3$— where Q is a group of the formula (VI).

Those compounds of the formula (I) are of interest, in which m+n is a number from 1 to 100, n is zero or a number from 1 to 50 and can vary from zero to 50% of the sum of m+n.

The preferred definitions of $R_7$ and $R_{11}$ are hydrogen, $C_1$-$C_4$alkyl, OH, $C_6$-$C_{12}$alkoxy, $C_5$-$C_8$cycloalkoxy, allyl, benzyl and acetyl, especially hydrogen or methyl.

Those components of the formula (I) are preferred in which $R_1$ is a group of the formula (II), X is —O— or >N—$R_{10}$, $R_{10}$ is hydrogen, $C_1$-$C_{12}$alkyl, $C_2$-$C_3$alkyl substituted in the 2- or 3-position by $C_1$-$C_4$alkoxy, by di-($C_1$-$C_4$alkyl)-amino or by a 1-pyrrolidyl, 1-piperidyl or 4-morpholinyl group; $C_5$-$C_8$cycloalkyl which is unsubstituted or mono-, di- or tri-substituted by $C_1$-$C_4$alkyl; benzyl, tetrahydrofurfuryl or a group of the formula (III), or X can also be a 1,4-piperazinediyl group or a group of the formula (IVa) or (IVb), $R_8$ is one of the groups of the formulae (Va)-(Vd) in which Z is as defined for X, and $R_{12}$, $R_{13}$ and $R_{14}$ which can be identical or different are hydrogen, $C_1$-$C_{12}$alkyl, $C_2$-$C_3$alkyl substituted in the 2- or 3-position by $C_1$-$C_4$alkoxy, by di-($C_1$-$C_4$alkyl)-amino or by a 1-pyrrolidyl, 1-piperidyl or 4-morpholinyl group; $C_5$-$C_8$cycloalkyl which is unsubstituted or mono-, di- or tri-substituted by $C_1$-$C_4$alkyl; $C_3$-$C_{12}$alkenyl, phenyl, benzyl or tetrahydrofurfuryl, or $R_{13}$ is OH or $C_1$-$C_4$alkoxy, or

is a 1-pyrrolidyl, 1-piperidyl, 4-morpholinyl or 1-hexahydroazepinyl group, $R_9$ is $C_1$-$C_6$alkylene or $C_5$-$C_9$alkylene interrupted by 1 or 2 groups of the formula (VI), Y is a group $>N$—$R_{15}$ with $R_{15}$ being hydrogen, $C_1$-$C_{12}$alkyl, $C_5$-$C_8$cycloalkyl which is unsubstituted or mono-, di- or tri-substituted by $C_1$-$C_4$alkyl; or benzyl, or Y, when $R_9$ is $C_1$-$C_6$alkylene, can also be —O— or —S—, $R_2$ is $C_1$-$C_6$alkyl, $C_1$-$C_6$alkoxy, OH, ONa or OK, $R_3$ and $R_4$ which can be identical or different are $C_1$-$C_6$alkyl or phenyl, m+n is a number from 1 to 50, n being zero or a number from 1 to 45 which can vary from zero to 90% of the sum of m+n, $R_5$ is hydrogen, $C_1$-$C_6$alkyl, Na, K or a group $(R_{16})_3$Si— with $R_{16}$ being $C_1$-$C_4$alkyl, and $R_6$ is $C_1$-$C_6$alkoxy, OH, ONa, OK or a group $(R_{16})_3$SiO— with $R_{16}$ as defined above and, when m+n is a number from 3 to 10, $R_5$ and $R_6$ together can also form a direct bond.

Those compounds of the formula (I) are particularly preferred in which $R_1$ is a group of the formula (II), X is —O— or $>N$—$R_{10}$, $R_{10}$ is hydrogen, $C_1$-$C_{10}$alkyl, $C_2$-$C_3$alkyl substituted in the 2- or 3-position by methoxy, by ethoxy, by dimethylamino, by diethylamino or by 4-morpholinyl; cyclohexyl which is unsubstituted or mono-, di- or tri-substituted by $C_1$-$C_4$alkyl; benzyl, tetrahydrofurfuryl or a group of the formula (III), or X can also be a group of the formula (IVa) or (IVb), $R_8$ is one of the groups of the formulae (Va)-(Vd) in which Z is as defined for X, and $R_{12}$, $R_{13}$ and $R_{14}$ which can be identical or different are $C_1$-$C_{10}$alkyl, $C_2$-$C_3$alkyl substituted in the 2- or 3-position by methoxy, by ethoxy, by dimethylamino, by diethylamino or by 4-morpholinyl; cyclohexyl which is unsubstituted or mono-, di- or tri-substituted by $C_1$-$C_4$alkyl; allyl, phenyl, benzyl or tetrahydrofurfuryl, or $R_{13}$ can also be hydrogen or OH, or

is a 4-morpholinyl group, $R_9$ is $C_1$-$C_4$alkylene or $C_5$-$C_7$alkylene interrupted by 1 or 2 groups of the formula (VI), Y is a group $>N$—$R_{15}$ with $R_{15}$ being hydrogen, $C_1$-$C_{10}$alkyl, cyclohexyl which is unsubstituted or mono-, di- or tri-substituted by $C_1$-$C_4$alkyl; or benzyl, or Y, when $R_9$ is $C_1$-$C_4$alkylene, can also be —O— or —S—, $R_2$ is $C_1$-$C_4$alkyl, $C_1$-$C_4$alkoxy, OH, ONA or OK, $R_3$ and $R_4$ which can be identical or different are $C_1$-$C_4$alkyl or phenyl, m+n is a number from 1 to 30, n being zero or a number from 1 to 27 which can vary from zero to 90% of the sum of m+n, $R_5$ is hydrogen, $C_1$-$C_4$alkyl, Na, K or a group $(CH_3)_3$Si— and $R_6$ is $C_1$-$C_4$alkoxy, OH, ONa, OK or a group $(CH_3)_3$SiO— and, when m+n is a number from 3 to 10, $R_5$ and $R_6$ together can also form a direct bond.

Those compounds of the formula (I) are of special interest in which $R_1$ is a group of the formula (II), X is —O— or $>N$—$R_{10}$, $R_{10}$ is hydrogen, $C_1$-$C_8$alkyl, cyclohexyl, benzyl, tetrahydrofurfuryl or a group of the formula (III), or X can also be a group of the formulae (IVa) or (IVb), $R_8$ is a group of the formula (Va) in which Z is as defined for X, $R_9$ is $C_2$-$C_4$alkylene or $C_5$-$C_6$alkylene interrupted by a group of the formula (VI), Y is a group $>N$—$R_{15}$ with $R_{15}$ being hydrogen, $C_1$-$C_8$alkyl, cyclohexyl or benzyl, or Y, when $R_9$ is $C_2$-$C_4$alkylene, can also be —O— or —S—, $R_2$ is $C_1$-$C_3$alkyl, $C_1$-$C_3$alkoxy or OH, $R_3$ and $R_4$ are methyl, m+n is a number from 1 to 20, n is zero or a number from 1 to 10 and can vary from zero to 50% of the sum of m+n, $R_5$ is hydrogen, $C_1$-$C_3$alkyl, Na, K or a group $(CH_3)_3$Si— and $R_6$ is $C_1$-$C_3$alkoxy, OH, ONa, OK or a group $(CH_3)_3$SiO— and, when m+n is a number from 3 to 10, $R_5$ and $R_6$ together can also form a direct bond.

Those compounds of the formula (I) are of particular interest in which $R_1$ is a group of the formula (II), $R_7$ is hydrogen or methyl, X is —O— or $>N$—$R_{10}$ with $R_{10}$ being $C_1$-$C_8$alkyl, 2,2,6,6,-tetramethyl-4-piperidyl or 1,2,2,6,6-pentamethyl-4-piperidyl, $R_8$ is a group of the formula (Va) with $R_{11}$ being hydrogen or methyl and Z being as defined above for X; Y is $>NH$, $R_9$ is trimethylene or a group—$(CH_2)_2$—Q—$(CH_2)_3$— where Q is a group of the formula (VI), $R_2$ is methyl, methoxy, ethoxy or OH, m is a number from 1 to 10, n is zero, $R_5$ is hydrogen, methyl or ethyl and $R_6$ is methoxy, ethoxy or OH and, when m is a number from 3 to 10, $R_5$ and $R_6$ together can also form a direct bond.

Those compounds of the formula (I) are also of particular interest, in which $R_1$ is a group of the formula (II), $R_7$ is hydrogen or methyl, X is $>N$—$R_{10}$ with $R_{10}$ being $C_1$-$C_4$alkyl, $R_8$ is a group of the formula (Va) with $R_{11}$ being hydrogen or methyl, and Z being as defined for X; Y is $>NH$, $R_9$ is trimethylene, $R_2$ methyl, ethoxy or OH, m is a number from 1 to 10, n is zero, $R_5$ is ethyl and $R_6$ is ethoxy and, when m is a number from 3 to 10, $R_5$ and $R_6$ together can also form a direct bond.

The compounds of the formula (I) can be prepared by various processes.

According to process A, when m is 1 and n is zero, the compounds of the formula (I) can be prepared e.g. by reacting, in the appropriate molar ratios, a chlorotriazine of the formula (VII)

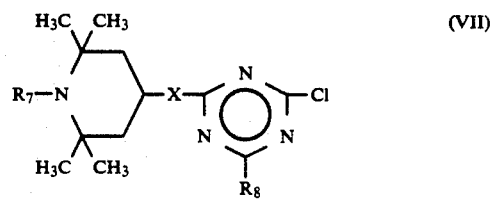

in which $R_7$, $R_8$ and X are as defined above, with a silane compound of the formula (VIII)

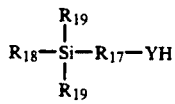

(VIII)

in which Y is as defined above, $R_{17}$ is $C_1$-$C_{12}$alkylene or $C_3$-$C_{15}$alkylene interrupted by 1 or 2>NH groups, $R_{18}$ is $C_1$-$C_8$alkyl or $C_1$-$C_8$alkoxy and $R_{19}$ is $C_1$-$C_8$alkoxy, operating under anhydrous conditions in a solvent such as a preferably secondary or tertiary $C_3$-$C_8$alcohol, dioxane, dibutyl ether, dimethoxyethane, diethoxyethane, bis-(2-methoxyethyl) ether or bis-(2-ethoxyethyl) ether, at temperatures between e.g. 80° and 200° C., preferably between e.g. 100° and 180° C.

In this reaction, the compounds of the formula (IX)

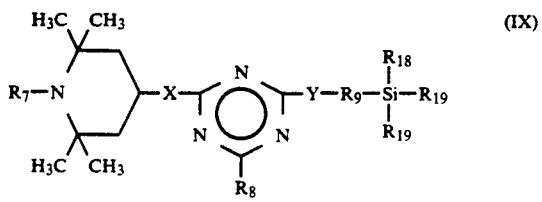

(IX)

are formed as the hydrochlorides, and the free bases of the compounds can be obtained after neutralization with a preferably inorganic base, such as sodium or potassium hydroxide or carbonate, at temperatures between e.g. 0° and 40° C., preferably between e.g. 10° and 25° C.

By total or partial hydrolysis of the compounds thus obtained, the corresponding silanol compounds containing 1, 2 or 3 OH groups bound to the silicon atom can be prepared, from which the corresponding compounds of the formula (I) with m being at least 2 and n being zero can be obtained by condesation reactions.

The hydrolysis and condensation reactions are preferably carried out simultaneously by treating the compounds of the formula (IX) with water in a quantity of least 0.5 mol per alkoxy group bound to the silicon atom, in the presence of a catalyst, for example acids, bases and salts of Zn, Fe, Pb, Sn or organotin compounds.

The preferred catalysts are inorganic acids, for example HCl, $H_2SO_4$ and $H_3PO_4$, and inorganic bases, for example NaOH and KOH, operating e.g. at temperatures between −10° and 150° C., preferably between 10° and 100° C., with the inorganic acids and between 40° and 200° C., preferably between 60° and 150° C., with the inorganic bases.

The hydrolysis/condensation reactions are preferably carried out in water or in the same solvent as that used for the preparation of the compounds of the formula (IX).

When m is at least 2 and n is other than zero, the compounds of the formula (I) can be prepared e.g. by hydrolysis/condensation of mixtures, in the appropriate ratios, of compounds of the formula (IX) and compounds of the formula (X)

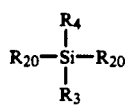

(X)

in which $R_3$ and $R_4$ are as defined above and $R_{20}$ is Cl or $C_1$-$C_8$alkoxy, operating under the conditions indicated above.

The compounds of the formula (I) with m>2 and n=0 or other than 0 can also be obtained directly from the hydrochloride of the compounds of the formula (IX) by hydrolysis/condensation in the same reactor in the presence of an inorganic acid or inorganic base, operating in the same reaction solvent or in water.

According to process B, when $R_9$ is trimethylene or 2-methyltrimethylene, the compounds of the formula (I) can also be prepared e.g. by reacting a compound of the formula (XI)

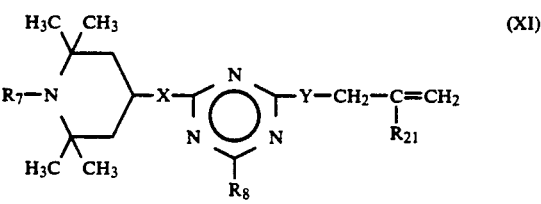

(XI)

with $R_{21}$ being hydrogen or methyl, with a compound of the formula (XIIa) or (XIIb)

(XIIA)

(XIIb)

in which $R_{18}$ and $R_{19}$ are as defined above and $R_{22}$ is Cl or $C_1$-$C_8$alkyl; the compounds of the formulae (XIIIa) and (XIIIb)

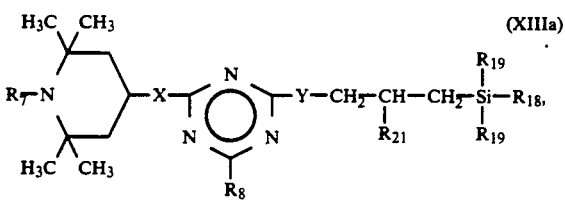

(XIIIa)

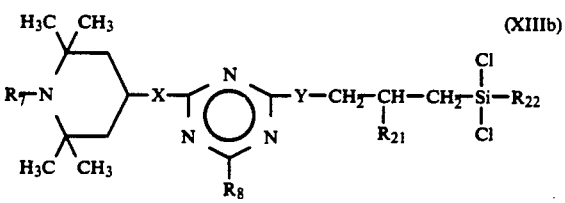

(XIIIb)

respectively being obtained which are then subjected to hydrolysis/condensation reactions, by themselves or as a mixture with the compounds of the formula (X), operating e.g. under the conditions indicated above for process A.

The addition reactions of the compounds of the formula (XI) with the compound of the formula (XIIa) or (XIIb) can be carried out e.g. in the presence of hydrosilylation catalyst such as Pd, Pt, Rh and derivatives thereof, preferably Pt and Rh complexes, in particular $H_2PtCl_6$ or $RhCl(Ph_3P)_3$, using an inert solvent such as hexane, heptane, dioxane, tetrahydrofuran, cyclohexane, toluene or xylene, at temperatures between e.g. 60° and 150° C., preferably between 80° and 120° C.

According to process C, when m is at least 2, n is zero or other than zero and $R_9$ is trimethylene or 2-methyltrimethylene, the compounds of the formula (I) can also be prepared e.g. by reacting, in the appropriate molar ratios, a compound of the formula (XI) with the compounds of the formula (XIV)

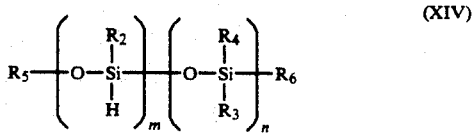
(XIV)

in which $R_2$, $R_3$, $R_4$, $R_5$, $R_6$, m and n are as defined above in the presence of a hydrosilylation catalyst as indicated above for process B.

According to process D, when m is at least 2 and n is zero or other than zero, the compounds of the formula (I) can also be prepared e.g. by reacting, in the appropriate molar ratios, a chlorotriazine of the formula (VII) with a compound of the formula (XV)

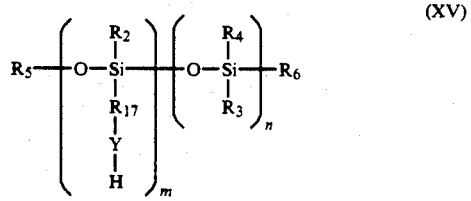
(XV)

in which $R_2$, $R_3$, $R_4$, $R_5$, $R_6$, $R_{17}$, Y, m and n are as defined above, operating under the conditions indicated above for process A.

In the hydrolysis/condensation reactions according to the various processes illustrated above, it is possible to use a compound of the formula $(R_{16})_3Si$—$R_{20}$, with $R_{16}$ and $R_{20}$ being as defined above, as a chain stopper. In this case, the terminal groups can be $(R_{16})_3SiO$— groups.

In the absence of the above chain stopper, the terminal groups can be e.g. $C_1$–$C_8$alkoxy, OH, ONa or OK as a function of the hydrolysis/condensation conditions and of the catalyst used.

The chlorotriazines of the formula (VII) can be prepared by known processes, for example as reported in U.S. Pat. No. 4,108,829.

The compounds of the formula (XI) can be prepared, for example, as described in European laid open print 101,411.

The compounds of the formulae (VIII), (X), (XIIa) (XIIb) and (XIV) are commercially available and easily obtainable by known processes.

The compounds of the formula (XV) can be prepared by hydrolysis/condensation of the compounds of the formula (VIII) by themselves or as a mixture with compounds of the formula (X).

As mentioned at the outset, the compounds of the formula (I) are highly effective in improving the light stability, and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, poly- methylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene and polyamides.

14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices. The compounds of the formula (I) can be incorporated into the material to be stabilized in a pure form or encapsulated in waxes, oils or polymers.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6- pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis-(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

Several examples of the preparation of the compounds of the formula (I) are reported for more detailed illustration of the present invention; these examples are given solely for illustrative purposes and do not imply any restriction. A preferred embodiment of the instant invention relates to examples 2, 7, 9, 12 and 13.

EXAMPLE 1

Preparation of the Compound of the Formula

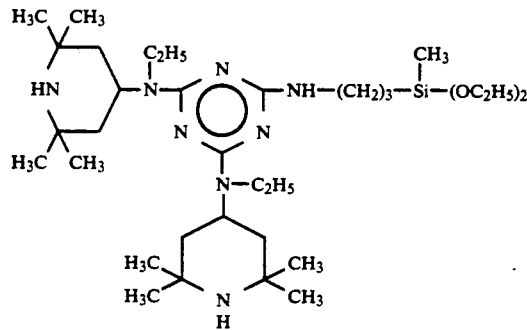

20.1 g (0.105 mol) of 3-(diethoxymethylsilyl)-propylamine are added in the course of 90 minutes to a solution, heated under reflux, of 48 g (0.1 mol) of 2-chloro-4,6-bis-[N-(2,2,6,6-tetramethyl-4-piperidyl)-ethylamino]-1,3,5-triazine in 300 ml of bis-(2-methoxyethyl) ether.

After the end of the addition, the mixture is heated under reflux for 4 hours, the solvent is then evaporated at reduced pressure, the residue is dissolved in 300 ml of dichloroethane and the resulting solution is treated for 15 minutes at ambient temperature with 24.2 g of a 33% aqueous sodium hydroxide solution.

After the aqueous phase has been separated off, the organic phase is washed with water, dehydrated with $Na_2SO_4$ and evaporated to dryness. The product obtained melts at 43°–48° C.

Analysis for $C_{33}H_{66}N_8O_2Si$: Calculated: C=62.42%; H=10.47%; N=17.65%. Found: C=62.73%; H=10.57%; N=17.47%.

EXAMPLES 2-5

Following the procedure described in Example 1 and using the respective reagents, the following compounds of the formula

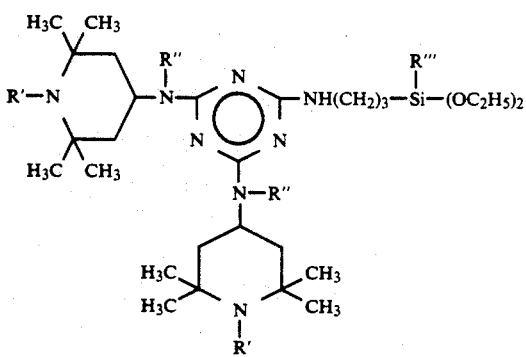

are prepared.

| Example | R' | R" | R'" | appearance |
|---|---|---|---|---|
| 2 | H | C₂H₅ | —OC₂H₅ | waxy |
| 3 | H | n—C₄H₉— | —CH₃ | soft resin |
| 4 | H | n—C₄H₉— | —OC₂H₅ | soft resin |
| 5 | CH₃ | n—C₄H₉— | —CH₃ | m.p. 40–44° C. |

EXAMPLE 6

Preparation of the Compound of the Formula

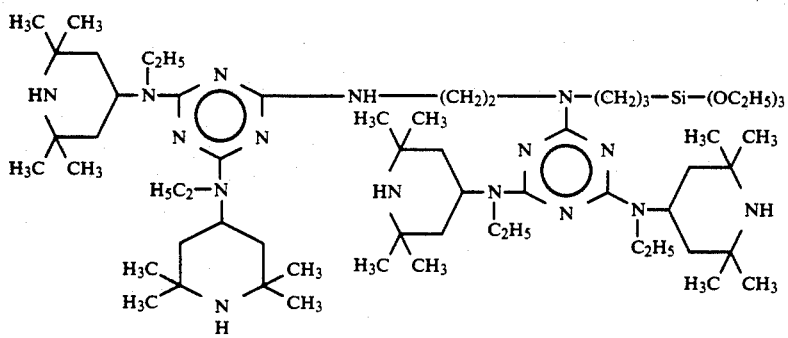

13.2 g (0.05 mol) of N-[3-(triethoxysilyl)-propyl]-ethylenediamine are reacted with 48 g (0.1 mol) of 2-chloro-4,6-bis-[N-(2,2,6,6-tetramethyl-4-piperidyl)e-thylamino]-1,3,5-triazine as described in Example 1. The product obtained melts at 79°–81° C.

Analysis for $C_{61}H_{118}N_{16}O_3Si$: Calculated: C=63.61%; H=10.32%; N=19.46%. Found: C=63.31%; H=10.47%; N=19.31%.

EXAMPLE 7

Preparation of a Polysiloxane Containing Recurring Units of the Formula

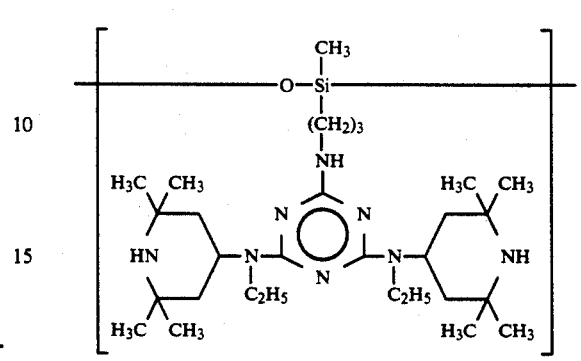

20.1 g (0.105 mol) of 3-(diethoxymethylsilyl)-propylamine are added in the course of 90 minutes to a solution, heated under reflux, of 48 g (0.1 mol) of 2-chloro-4,6-bis-[N-(2,2,6,6-tetramethyl-4-piperidyl)-ethylamino]-1,3,5-triazine in 300 ml of bis-(2-methoxyethyl) ether.

After the end of the addition, the mixture is heated under reflux for 4 hours, the solvent is then evaporated under reduced pressure and the residue is dissolved in 240 ml of 1N HCl. The solution is stirred for 2 hours at ambient temperature and then treated with a solution of 15 g of sodium hydroxide in 50 ml of water for 1 hour at ambient temperature.

The precipitate which has formed is separated off by filtration, washed with water until neutral and dried. The product obtained has a melting point of 123°–126° C. and a molecular weight of $\overline{M}n=2200$.

EXAMPLE 8

The same polysiloxane as in Example 7 is prepared by reacting 0.105 mol of 3-(diethoxymethylsilyl)-propylamine with 0.1 mol of 2-chloro-4,6-bis-[N-(2,2,6,6-tetramethyl-4-piperidyl)-ethylamino]-1,3,5-triazine as described in Example 7, adding 13.5 g of 33% aqueous sodium hydroxide solution to the organic solution after the end of the reaction and heating for 2 hours at 120° C. After cooling to ambient temperature and separating off the aqueous phase, the solvent is evaporated under reduced pressure and the residue is washed with water and dried.

The product obtained has a melting point of 116°–119° C. and a molecular weight of $\overline{M}n=2170$.

EXAMPLE 9

Following the procedure described in Example 7 and using the respective reagents, a polysiloxane containing recurring units of the formula

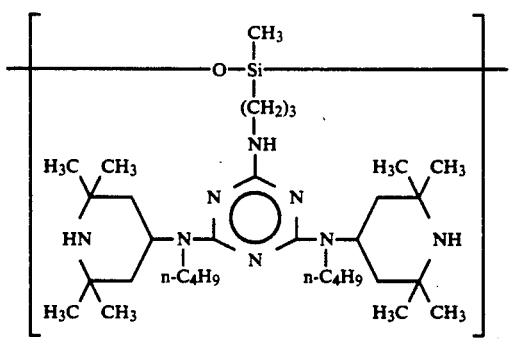

having a melting point of 108°–115° C. and a molecular weight of $\overline{M}n=2800$ is prepared.

EXAMPLE 10

Following the procedure described in Example 8 and using the respective reagents, a polysiloxane containing recurring units of the formula

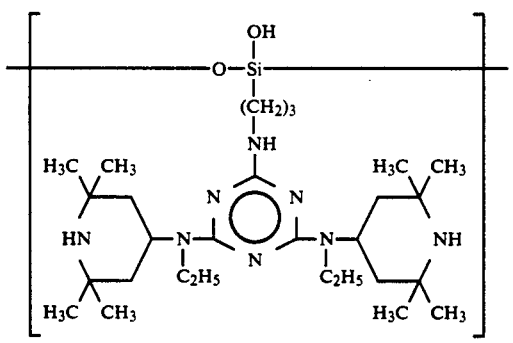

and having a melting point of 147°–150° C. and a molecular weight of $\overline{M}n=3680$ is prepared.

EXAMPLE 11

Preparation of a polysiloxane containing recurring units of the formula

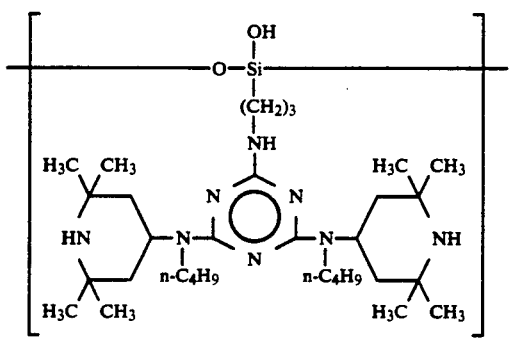

22.1 g (0.105 mol) of 3-(triethoxysilyl)-propylamine are added in the course of 90 minutes to a solution, heated under reflux, of 53.6 g (0.1 mol) of 2-chloro-4,6-bis-[N-(2,2,6,6-tetramethyl-4-piperidyl)-butylamino]-1,3,5-triazine in 300 ml of bis-(2-methoxyethyl)ether.

After the end of the addition, the mixture is heated under reflux for 4 hours and the solvent is then evaporated under reduced pressure; the residue is dissolved in 200 ml of 0.5N HCl and the solution is heated under reflux for 4 hours. After cooling to ambient temperature, a solution of 8.8 g of sodium hydroxide in 50 ml of water is added and the mixture is stirred for 1 hour at ambient temperature.

The precipitate which has formed is separated off by filtration, washed with water until neutral and dried. The product obtained has a melting point of 130°–134° C. and a molecular weight of $\overline{M}n=5500$.

EXAMPLE 12

The same compound as in Example 11 but having a molecular weight of $\overline{M}n=3050$ is prepared by reacting 0.105 mol of 3-(triethoxysilyl)-propylamine with 0.1 mol of 2-chloro-4,6-bis-[N-(2,2,6,6-tetramethyl-4-piperidyl)-butylamino]-1,3,5-triazine as described in Example 11, adding 4.0 g of 33% aqueous sodium hydroxide solution to the organic solution after the end of the reaction and heating for 8 hours at 120° C.

After cooling to ambient temperature and separating off the aqueous phase, the solvent is evaporated under reduced pressure and the residue is washed with water and dried.

The product obtained has a melting point of 136°–139° C.

EXAMPLE 13

Preparation of a Polysiloxane Containing Recurring Units of the Formula

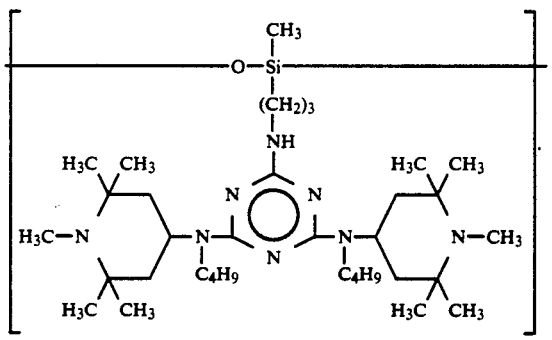

20.1 g (0.105 mol) of 3-(diethoxymethylsilyl)-propylamine are added in the course of 90 minutes to a solution, heated under reflux, of 56.4 g (0.1 mol) of 2-chloro-4,6-bis-[N-(1,2,2,6,6-pentamethyl-4-piperidyl)-butylamino]-1,3,5-triazine in 300 ml of bis-(2-methoxyethyl)ether.

After the end of the addition, the mixture is heated under reflux for 4 hours, the solvent is then evaporated under reduced pressure and the residue is dissolved in 240 ml of 1N HCl.

The solution is heated 4 hours under reflux, cooled to ambient temperature and treated with a solution of 15 g of sodium hydroxide in 50 ml of water for 1 hour.

The precipitate which has formed is separated off by filtration, washed with water until neutral and dried.

The product obtained has a melting point of 113°–116° C. and a molecular weight of $\overline{M}n=2600$.

In the examples, the number-average molecular weight is determined by means of a vapour pressure osmometer (®Gonotec) as described in EP-A-255,990, page 18, line 54, to page 19, line 15.

The efficacy of the compounds of the present invention as stabilizers is illustrated in the following examples in which several compounds obtained in the preparation examples are used for stabilizing the polypropylene fibres, tapes and plaques.

EXAMPLE 14

Light-Stabilizing Action in Polypropylene Fibres 2.5 g of each of the products indicated in Table 1, 1.0 g of tris-(2,4-di-t-butylphenyl)phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°-230° C. to give polymer granules which are then converted into fibres, using a pilot-type apparatus (®Leonard, Sumirago (VA), Italy) operating under the following conditions:
  extruder temperature: 200°-230° C.
  head temperature: 255°-260° C.
  stretch ratio: 1:3.5
  count: 11 dtex per filament The fibres thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of the compounds of the invention, are exposed for comparison.

The results obtained are shown in Table 1:

TABLE 1

| Stabilizer | $T_{50}$ (hours) |
|---|---|
| None | 150 |
| Compound from Example 1 | 1500 |
| Compound from Example 2 | 1600 |
| Compound from Example 3 | 1400 |
| Compound from Example 4 | 1420 |
| Compound from Example 5 | 1420 |
| Compound from Example 9 | 1470 |
| Compound from Example 12 | 1600 |

EXAMPLE 15

Light-Stabilizing Action in Polypropylene Tapes 1 g of each of the compounds indicated in Table 2, 1.0 g of tris-(2,4-di-t-butylphenyl) phosphite, 0.5 g of pentaerythritol tetrakis-[3-(3,5-di-t-butyl-4-hydroxyphenyl)-propionate] and 1 g of calcium stearate are mixed in a slow mixer with 1000 g of polypropylene powder of melt index=2 g/10 minutes (measured at 230° C. and 2.16 kg).

The mixtures are extruded at 200°-230° C. to give polymer granules which are then converted into stretched tapes of 50 μm thickness and 2.5 mm width, using a pilot-type apparatus (®Leonard-Sumirago (VA), Italy) operating under the following conditions:
  Extruder temperature: 210°-230° C.
  Head temperature: 240°-260° C.
  Stretch ratio: 1:6

The tapes thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer; the exposure time (in hours) ($T_{50}$) needed to halve the initial tenacity is then calculated.

Tapes prepared under the same conditions as indicated above, but without addition of stabilizer, are exposed for comparison.

The results obtained are shown in Table 2.

TABLE 2

| Stabilizer | $T_{50}$ (hours) |
|---|---|
| None | 300 |
| Compound from Example 1 | 2950 |
| Compound from Example 2 | 2920 |
| Compound from Example 3 | 2900 |
| Compound from Example 9 | 3100 |
| Compound from Example 10 | 2900 |
| Compound from Example 12 | 3020 |

EXAMPLE 16

Antioxidant Action in Polypropylene Plaques 1 g of each of the compounds indicated in Table 3, 0.5 g of octadecyl 3-(3,5-di-t-butyl-4-hydroxyphenyl)-propionate, 1 g of tris-(2,4-di-t-butylphenyl)phosphite and 1 g of calcium stearate are mixed in a slow mixer with 1000 g of polypropylene powder of melt index=2 g/10 minutes (measured at 230° C. and 2.16 kg).

The mixtures are extruded twice at 200°-230° C. to give polymer granules which are then converted into plaques of 1 mm thickness by compression-moulding for 6 minutes at 230° C.

The plaques are then punched by means of a DIN 53 451 mould, and the specimens obtained are exposed in a forced-circulation air oven maintained at a temperature of 135° C.

The specimens are checked at intervals by folding them by 180°, in order to determine the time (in hours) needed to cause fracture. Specimens prepared under the conditions indicated above, but without addition of the compounds of the present invention, are also exposed for comparison.

The results obtained are shown in Table 3.

TABLE 3

| Stabilizer | Time of fracture (hours) |
|---|---|
| None | 550 |
| Compound from Example 5 | 1900 |
| Compound from Example 7 | 1950 |
| Compound from Example 9 | 1890 |
| Compound from Example 13 | 2050 |

The compounds of formula (I) can also be used as stabilizers, especially as light stabilizers, for almost all materials known in the art of photographic reproduction and other reproduction techniques as e.g. described in Research Disclosure 1990, 31429 (pages 474 to 480).

What is claimed is:

1. A compound of the formula (I)

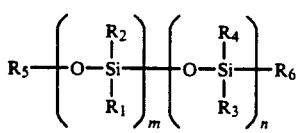 (I)

in which $R_1$ is a group of the formula (II)

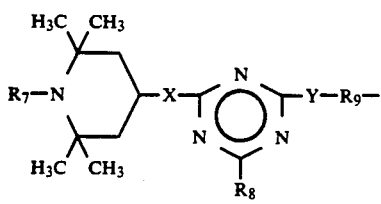 (II)

where $R_7$ is hydrogen, $C_1$–$C_8$alkyl, O, OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl; or $C_1$–$C_8$acyl, X is —O— or >N—$R_{10}$, where $R_{10}$ is hydrogen, $C_1$–$C_{18}$alkyl, $C_2$–$C_4$alkyl substituted in the 2-, 3- or 4-position by $C_1$–$C_8$alkoxy, by di-($C_1$–$C_4$alkyl)-amino or by a 5-membered to 7-membered nitrogen containing heterocyclic group with the free valency on the nitrogen atom; $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; tetrahydrofurfuryl or a group of the formula (III)

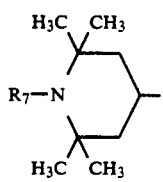 (III)

with $R_7$ as defined above, or X can also be a 1,4-piperazinediyl group or a group of the formula (IVa) or (IVb)

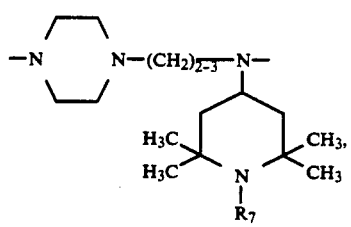 (IVa)

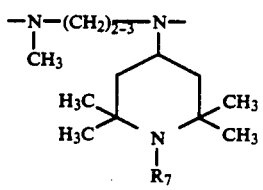 (IVb)

with $R_7$ as defined above and the nitrogen atom substituted by the piperidyl group being bound to the triazine ring of the group of the formula (II), $R_8$ is one of the groups of the formulae (Va)–(Vd)

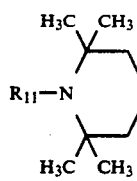 (Va)

 (Vb)

 (Vc)

 (Vd)

in which $R_{11}$ is as defined for $R_7$, Z is as defined for X, and $R_{12}$, $R_{13}$ and $R_{14}$ which can be identical or different are hydrogen, $C_1$–$C_{18}$alkyl, $C_2$–$C_4$alkyl substituted in the 2-, 3- or 4-position by $C_1$–$C_8$alkoxy, by di-($C_1$–$C_4$alkyl)-amino or by a 5-membered to 7-membered nitrogen containing heterocyclic group with the free valency on the nitrogen atom; $C_5$–$C_{12}$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; $C_7$–$C_9$phenylalkyl which is unsubstituted or mono-, di- or tri-substituted on the phenyl by $C_1$–$C_4$alkyl; or tetrahydrofurfuryl, or $R_{13}$ is OH or $C_1$–$C_8$alkoxy or

is a 5-membered to 7-membered heterocyclic group, $R_9$ is $C_1$–$C_{12}$alkylene or $C_5$–$C_{15}$alkylene interrupted by 1 or 2 groups of the formula (VI)

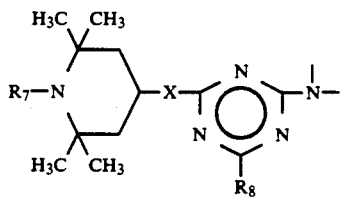 (VI)

with $R_7$, $R_8$ and X as defined above and Y is a group >N—$R_{15}$ where $R_{15}$ is hydrogen, $C_1$–$C_{18}$alkyl, $C_5$–$C_{12}$cycloalkyl which is unsubstituted or mono-, di- or tri-substituted by $C_1$–$C_4$alkyl; or $C_7$–$C_9$phenylalkyl which is unsubstituted or mono-, di- or tri-substituted on the phenyl by $C_1$–$C_4$alkyl; or Y, when $R_9$ is $C_1$–$C_{12}$alkylene, can also be —O— or —S—, $R_2$ is $C_1$–$C_8$alkyl, $C_1$–$C_8$alkoxy, OH, ONa or OK, $R_3$ and $R_4$ which can be identical or different are $C_1$–$C_8$alkyl or phenyl, m+n is a number from 1 to 100, n is zero or a number from 1 to 90 and can vary from zero to 90% of the sum of m+n, $R_5$ is hydrogen, $C_1$–$C_8$alkyl, Na, K or a group $(R_{16})_3Si$— with $R_{16}$ being $C_1$–$C_8$alkyl, and $R_6$ is $C_1$–$C_8$alkoxy, OH, ONa, OK or a group $(R_{16})_3SiO$— with $R_{16}$ as defined above and, when m+n is a number from 3 to 10, $R_5$ and $R_6$ together can also form a direct bond; each of the groups $R_1$, $R_2$, $R_3$ and $R_4$ can have the same definition or different definitions in the recurring structural units contained in formula (I) and, when the compounds of the formula (I) are copolymeric, they can have a random distribution or a block distribution of the individual structural units.

2. A compound of the formula (I) according to claim 1, in which m+n is a number from 1 to 100, n is zero or a number from 1 to 50 and can vary from zero to 50% of the sum of m+n.

3. A compound of the formula (I) according to claim 1, in which $R_7$ and $R_{11}$ which can be identical or different are hydrogen, $C_1$-$C_4$alkyl, OH, $C_6$-$C_{12}$alkoxy, $C_5$-$C_8$cycloalkoxy, allyl, benzyl or acetyl.

4. A compound of the formula (I) according to claim 1, in which $R_1$ is a group of the formula (II), X is —O— or >N—$R_{10}$, $R_{10}$ is hydrogen, $C_1$-$C_{12}$alkyl, $C_2$-$C_3$alkyl substituted in the 2- or 3-position by $C_1$-$C_4$alkoxy, by di-($C_1$-$C_4$alkyl)-amino or by a 1-pyrrolidyl, 1-piperidyl or 4-morpholinyl group; $C_5$-$C_8$cycloalkyl which is unsubstituted or mono-, di-or tri-substituted by $C_1$-$C_4$alkyl; benzyl, tetrahydrofurfuryl or a group of the formula (III), or X can also be a 1,4-piperazinediyl group or a group of the formula (IVa) or (IVb), $R_8$ is one of the groups of the formulae (Va)–(Vd) in which Z is as defined for X, and $R_{12}$, $R_{13}$ and $R_{14}$ which can be identical or different are hydrogen, $C_1$-$C_{12}$alkyl, $C_2$-$C_3$alkyl substituted in the 2- or 3-position by $C_1$-$C_4$alkoxy, by di-($C_1$-$C_4$alkyl)-amino or by a 1-pyrrolidyl, 1-piperidyl or 4-morpholinyl group; $C_5$-$C_8$cycloalkyl which is unsubstituted or mono-, di- or tri-substituted by $C_1$-$C_4$alkyl; $C_3$-$C_{12}$alkenyl, phenyl, benzyl or tetrahydrofurfuryl, or $R_{13}$ is OH or $C_1$-$C_4$alkoxy, or

is a 1-pyrrolidyl, 1-piperidyl, 4-morpholinyl or 1-hexahydroazepinyl group, $R_9$ is $C_1$-$C_6$alkylene or $C_5$-$C_9$alkylene interrupted by 1 or 2 groups of the formula (VI), Y is a group >N—$R_{15}$ with $R_{15}$ being hydrogen, $C_1$-$C_{12}$alkyl, $C_5$-$C_8$cycloalkyl which is unsubstituted or mono-, di- or tri-substituted by $C_1$-$C_4$alkyl; or benzyl, or Y, when $R_9$ is $C_1$-$C_6$alkylene, can also be —O— or —S—, $R_2$ is $C_1$-$C_6$alkyl, $C_1$-$C_6$alkoxy, OH, ONa or OK, $R_3$ and $R_4$ which can be identical or different are $C_1$-$C_6$alkyl or phenyl, m+n is a number from 1 to 50, n being zero or a number from 1 to 45 which can vary from zero to 90% of the sum of m+n, $R_5$ is hydrogen, $C_1$-$C_6$alkyl, Na, K or a group $(R_{16})_3$Si— with $R_{16}$ being $C_1$-$C_4$alkyl, and $R_6$ is $C_1$-$C_6$alkoxy, OH, ONa, OK or a group $(R_{16})_3$SiO— with $R_{16}$ as defined above and, when m+n is a number from 3 to 10, $R_5$ and $R_6$ together can also form a direct bond.

5. A compound of the formula (I) according to claim 1, in which $R_1$ is a group of the formula (II), X is —O— or >N—$R_{10}$, $R_{10}$ is hydrogen, $C_1$-$C_{10}$alkyl, $C_2$-$C_3$alkyl substituted in the 2- or 3-position by methoxy, by ethoxy, by dimethylamino, by diethylamino or by 4-morpholinyl; cyclohexyl which is unsubstituted or mono-, di-or tri-substituted by $C_1$-$C_4$alkyl; benzyl, tetrahydrofurfuryl or a group of the formula (III), or X can also be a group of the formula (IVa) or (IVb), $R_8$ is one of the groups of the formulae (Va)–(Vd) in which Z is as defined for X, and $R_{12}$, $R_{13}$ and $R_{14}$ which can be identical or different are $C_1$-$C_{10}$alkyl, $C_2$-$C_3$alkyl substituted in the 2- or 3-position by methoxy, by ethoxy, by dimethylamino, by diethylamino or by 4-morpholinyl; cyclohexyl which is unsubstituted or mono-, di- or tri-substituted by $C_1$-$C_4$alkyl; allyl, phenyl, benzyl or tetrahydrofurfuryl, or $R_{13}$ can also be hydrogen or OH, or

is a 4-morpholinyl group, $R_9$ is $C_1$-$C_4$alkylene or $C_5$-$C_7$alkylene interrupted by 1 or 2 groups of the formula (VI), Y is a group >N—$R_{15}$ with $R_{15}$ being hydrogen, $C_1$-$C_{10}$alkyl, cyclohexyl which is unsubstituted or mono-, di- or tri-substituted by $C_1$-$C_4$alkyl; or benzyl, or Y, when $R_9$ is $C_1$-$C_4$alkylene, can also be —O— or —S—, $R_2$ is $C_1$-$C_4$alkyl, $C_4$alkoxy, OH, ONa or OK, $R_3$ and $R_4$ which can be identical or different are $C_1$-$C_4$alkyl or phenyl, m+n is a number from 1 to 30, n being zero or a number from 1 to 27 which can vary from zero to 90% of the sum of m+n, $R_5$ is hydrogen, $C_1$-$C_4$alkyl, Na, K or a group $(CH_3)_3$Si— and $R_6$ is $C_1$-$C_4$alkoxy, OH, ONa, OK or a group $(CH_3)_3$SiO— and, when m+n is a number from 3 to 10, $R_5$ and $R_6$ together can also form a direct bond.

6. A compound of the formula (I) according to claim 1, in which $R_1$ is a group of the formula (II), X is —O— or >N—$R_{10}$, $R_{10}$ is hydrogen, $C_1$-$C_8$alkyl, cyclohexyl, benzyl, tetrahydrofurfuryl or a group of the formula (III), or X can also be a group of the formulae (IVa) or (IVb), $R_8$ is a group of the formula (Va) in which Z is as defined for X, $R_9$ is $C_2$-$C_4$alkylene or $C_5$-$C_6$alkylene interrupted by a group of the formula (VI), Y is a group >N—$R_{15}$ with $R_{15}$ being hydrogen, $C_1$-$C_8$alkyl, cyclohexyl or benzyl, or Y, when $R_9$ is $C_2$-$C_4$alkylene, can also be —O— or —S—, $R_2$ is $C_1$-$C_3$alkyl, $C_1$-$C_3$alkoxy or OH, $R_3$ and $R_4$ are methyl, m+n is a number from 1 to 20, n is zero or a number from 1 to 10 and can vary from zero to 50% of the sum of m+n, $R_5$ is hydrogen, $C_1$-$C_3$alkyl, Na, K or a group $(CH_3)_3$Si— and $R_6$ is $C_1$-$C_3$alkoxy, OH, ONa, OK or a group $(CH_3)_3$SiO— and, when m+n is a number from 3 to 10, $R_5$ and $R_6$ together can also form a direct bond.

7. A compound of the formula (I) according to claim 1, in which $R_1$ is a group of the formula (II), $R_7$ is hydrogen or methyl, X is —O— or >N—$R_{10}$ with $R_{10}$ being $C_1$-$C_8$alkyl, 2,2,6,6-tetramethyl-4-piperidyl or 1,2,2,6,6-pentamethyl-4-piperidyl, $R_8$ is a group of the formula (Va) with $R_{11}$ being hydrogen or methyl and Z being as defined above for X; Y is >NH, $R_9$ is trimethylene or a group —$(CH_2)_2$—Q—$(CH_2)_3$— where Q is a group of the formula (VI), $R_2$ is methyl, methoxy, ethoxy or OH, m is a number from 1 to 10, n is zero, $R_5$ is hydrogen, methyl or ethyl and $R_6$ is methoxy, ethoxy or OH and, when m is a number from 3 to 10, $R_5$ and $R_6$ together can also form a direct bond.

8. A compound of the formula (I) according to claim 1, in which $R_1$ is a group of the formula (II), $R_7$ is hydrogen or methyl, X is >N—$R_{10}$ with $R_{10}$ being $C_1$-$C_4$alkyl, $R_8$ is a group of the formula (Va) with $R_{11}$ being hydrogen or methyl and Z being as defined for X; Y is >NH, $R_9$ is trimethylene, $R_2$ is methyl, ethoxy or OH, m is a number from 1 to 10, n is zero, $R_5$ is ethyl and $R_6$ is ethoxy and, when m is a number from 3 to 10, $R_5$ and $R_6$ together can also form a direct bond.

* * * * *